(12) United States Patent
Newby (10) Patent No.: US 6,932,803 B2
(45) Date of Patent: Aug. 23, 2005

(54) NEEDLE DEVICE

(75) Inventor: C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 334 days.

(21) Appl. No.: 10/392,124

(22) Filed: Mar. 19, 2003

(65) Prior Publication Data

US 2003/0181872 A1 Sep. 25, 2003

Related U.S. Application Data

(60) Provisional application No. 60/365,506, filed on Mar. 19, 2002.

(51) Int. Cl.⁷ .............................................. A61M 31/00
(52) U.S. Cl. ...................... 604/500; 604/198; 604/162; 604/263; 604/110; 604/164.08
(58) Field of Search .................................. 604/198, 197, 604/162, 174, 192, 263, 110, 177, 93.01, 158, 500, 164.01, 164.08, 165.01–165.04, 168.01; 128/DIG. 26, DIG. 6, 919

(56) References Cited

U.S. PATENT DOCUMENTS

| 4,790,828 A | 12/1988 | Dombrowski et al. |
| 5,061,250 A | * 10/1991 | Shields ........................ 604/198 |
| 5,085,639 A | 2/1992 | Ryan |
| 5,088,982 A | 2/1992 | Ryan |
| 5,112,311 A | 5/1992 | Utterberg et al. |
| 5,120,320 A | 6/1992 | Fayngold |
| 5,154,699 A | 10/1992 | Ryan |
| 5,176,655 A | 1/1993 | McCormick et al. |
| 5,192,275 A | 3/1993 | Burns |
| 5,266,072 A | 11/1993 | Utterberg et al. |
| 5,290,264 A | 3/1994 | Utterberg |
| 5,350,368 A | * 9/1994 | Shields ........................ 604/263 |
| 5,401,250 A | * 3/1995 | Shields ........................ 604/192 |
| 5,423,766 A | 6/1995 | DiCesare |
| 5,562,636 A | 10/1996 | Utterberg |
| 5,562,637 A | 10/1996 | Utterberg |
| 5,704,917 A | * 1/1998 | Utterberg ..................... 604/180 |
| 5,704,924 A | * 1/1998 | Utterberg et al. ............ 604/263 |
| 5,735,827 A | 4/1998 | Adwers et al. |
| 5,951,525 A | 9/1999 | Thorne et al. |
| 6,280,420 B1 | 8/2001 | Ferguson et al. |
| 6,719,731 B2 | * 4/2004 | Parmigiani ................... 604/192 |
| 2001/0039401 A1 | 11/2001 | Ferguson et al. |
| 2003/0036731 A1 | * 2/2003 | Wilkinson et al. ........... 604/198 |
| 2004/0102739 A1 | * 5/2004 | Nakajima ..................... 604/263 |
| 2005/0070849 A1 | * 3/2005 | Yang ....................... 604/165.03 |

FOREIGN PATENT DOCUMENTS

| EP | 1 116 493 A1 | 7/2001 |
| JP | 8-206195 | 8/1996 |

* cited by examiner

*Primary Examiner*—Cris L. Rodriguez (57) ABSTRACT

The present invention is directed to a shieldable blood collection set and a needle assembly for use therewith. The needle assembly includes a needle cannula having a puncture tip at a distal end, a hub which supports the needle cannula, and a shield. The hub and the shield are axially movable with respect to each other between a first sampling position, where the puncture tip is exposed from the shield, and a second shielded position where the shield covers the puncture tip. A gauze pad is connected to the shield through a tether. After a venipuncture procedure, the gauze is maintained over the needle puncture tip at the puncture site, and the needle is withdrawn from the patient by pulling on the hub. This movement causes the tether to tightly extend between the gauze and the shield, which causes the needle puncture tip to be withdrawn into the shield.

20 Claims, 7 Drawing Sheets

NEEDLE DEVICE

CROSS REFERENCE TO RELATED APPLICATIONS

This application claims the benefit of U.S. Provisional Application No. 60/365,506 filed on Mar. 19, 2002.

BACKGROUND OF THE INVENTION

1. Field of the Invention

The present invention relates to blood collection sets for safe and convenient handling of needles. More particularly, the present invention relates to a blood collection set including a needle assembly having a needle cannula which is retractable within a safety shield for protection from a used needle tip.

2. Description of Related Art

Disposable medical devices having medical needles are used for administering medication or withdrawing fluid from the body of a patient. Such disposable medical devices typically include blood collecting needles, fluid handling needles, and assemblies thereof. Current medical practice requires that fluid containers and needle assemblies used in such devices be inexpensive and readily disposable. Consequently, existing blood collection devices typically employ some form of durable, reusable holder on which detachable and disposable medical needles and fluid collection tubes may be mounted. A blood collection device of this nature may be assembled prior to use and then disassembled after use. Thus, these blood collection devices allow repeated use of a relatively expensive holder upon replacement of relatively inexpensive medical needles and/or fluid collection tubes. In addition to reducing the cost of collecting blood specimens, these blood collection devices help minimize the production of hazardous waste material.

A blood collection device or intravenous "IV" infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tube is connected to the hub and communicates with the lumen of the needle cannula. The end of the plastic tube remote from the needle cannula may include a fixture for connecting the needle cannula to a blood collection tube or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies commonly employ a safety shield that can be moved into shielding engagement with a used needle cannula to minimize risk of an accidental needle-stick.

For example, U.S. Pat. No. 5,120,320 to Fayngold discloses an intravenous infusion set or a blood collection assembly with an automatic safety feature incorporating a needle cannula and a safety shield, in which the needle cannula can be pulled rearwardly such that the shield can be extended over the puncture tip of the needle. The assembly further includes flexible wings which can be used as means for securing the needle assembly to the skin of a patient during a medical procedure. U.S. Pat. No. 5,951,525 to Thome et al. discloses a manually operated safety needle apparatus that includes two pairs of opposed legs adapted to move a shield of the apparatus to a position covering the used needle cannula. U.S. Pat. Nos. 5,266,072, 5,433,703, 5,562,636 and 5,704,924 to Utterberg et al. each disclose a winged needle assembly with a shield that can be extended over the needle after use through a stiff elongated anchor portion which can be grasped by the user to shield the needle. The disclosure of each of these patents is incorporated herein by reference thereto.

Typically, after completion of a medical procedure involving such assemblies, the medical practitioner will cover the puncture wound at the site of insertion with a gauze pad and apply pressure with one hand while withdrawing the needle assembly from the site with the other hand. Accordingly, needle assemblies in which the shielding mechanism can be activated with a single hand have more recently been developed. Such assemblies, however, often require extensive mechanics for activation of the shield over the needle cannula. This results in complex arrangements that are costly to manufacture and assemble. Additionally, operation of the needle assemblies to move the tip guard into the proper position over the pointed distal end of the needle cannula requires substantial manual manipulation by the user of the device, exposing the user to potential needle-stick wounds.

In view of the foregoing, a need exists for a blood collection set including a shieldable needle assembly that achieves secure and effective shielding of a used needle cannula which is simple and inexpensive to manufacture and easy to operate.

SUMMARY OF THE INVENTION

The present invention is directed to a shieldable blood collection set as well as a needle assembly for use in a blood collection set. The needle assembly includes a needle cannula having a proximal end and a distal end with a puncture tip, with a hub member, having a proximal end and a distal end, supporting the proximal end of the needle cannula. The needle cannula further includes a shield member extending co-axially about the needle cannula. The shield member and the hub member are axially movable with respect to each other between a first position in which the needle assembly is in a sampling state with the puncture tip of the needle cannula exposed from the shield member, and a second position in which the needle assembly is in a shielded state with the needle cannula contained within the shield member such that the shield member covers the puncture tip of the needle cannula. The needle assembly also includes a gauze member, such as a gauze pad, extending from and connected to the shield member through a connecting member, such as a tether. When the shield member is in the first position and the gauze member is positioned adjacent the puncture tip, the connecting member is extendable to a taut position. Movement of the hub member away from the gauze member when the connecting member is extended to this taut position causes relative movement between the shield member and the hub member, from the first position to the second position. As such, the puncture tip of the needle cannula is effectively shielded within the shield member.

Desirably, the gauze member is removably connected to the shield member, such as by providing the tether attached to the shield member through a breakable bond. In this manner, the gauze member can be removed and maintained at the puncture wound of a patient after the needle cannula has been withdrawn from the patient.

Desirably, the needle assembly further includes means or structure for preventing the shield member from extending beyond the puncture tip. For example, the needle assembly may include at least one, and preferably a pair of, extendable members interconnecting the hub member and the shield member. The extendable members may each include a pair of folding legs connected by a hinged knee joint, with one leg of the pair of legs for each extendable member hingedly connected to the hub member and the other leg of the pair of legs for each of the extendable members hingedly connected to the shield member.

The needle assembly may also include means or structure for preventing the shield member from moving in an axial direction between the extended position and the retracted position, such as a locking assembly, or a tip guard assembly.

In a further embodiment, the present invention includes a shieldable blood collection set having a fixture for connecting the blood collection set to a receptacle; a flexible tube having opposed first and second ends, with the first end of the flexible tube being connected to the fixture; and a needle assembly as described above, with the hub of the needle assembly including an elongated tubular body mounted to the second end of the flexible tube.

Further, the present invention includes a method for shielding a puncture tip in a needle assembly. The method includes providing a needle assembly including a hub member having a needle cannula extending therefrom, with the needle cannula having a puncture tip at the end thereof; a shield member extending co-axially about the needle cannula, with the shield member and the hub member axially movable with respect to each other; and a gauze member extending from and connected to the shield member through a connecting member. The gauze member is maintained in a position adjacent the puncture tip while the hub member is simultaneously moved in an axial direction away from the gauze member. This movement causes the connecting member to be extended to a taut position, which causes the hub member and the needle cannula to axially move with respect to the shield member from a first position in which the puncture tip of the needle cannula is exposed from the shield member to a second position in which the shield member covers the puncture tip of the needle cannula.

DETAILED DESCRIPTION

Figure 6:
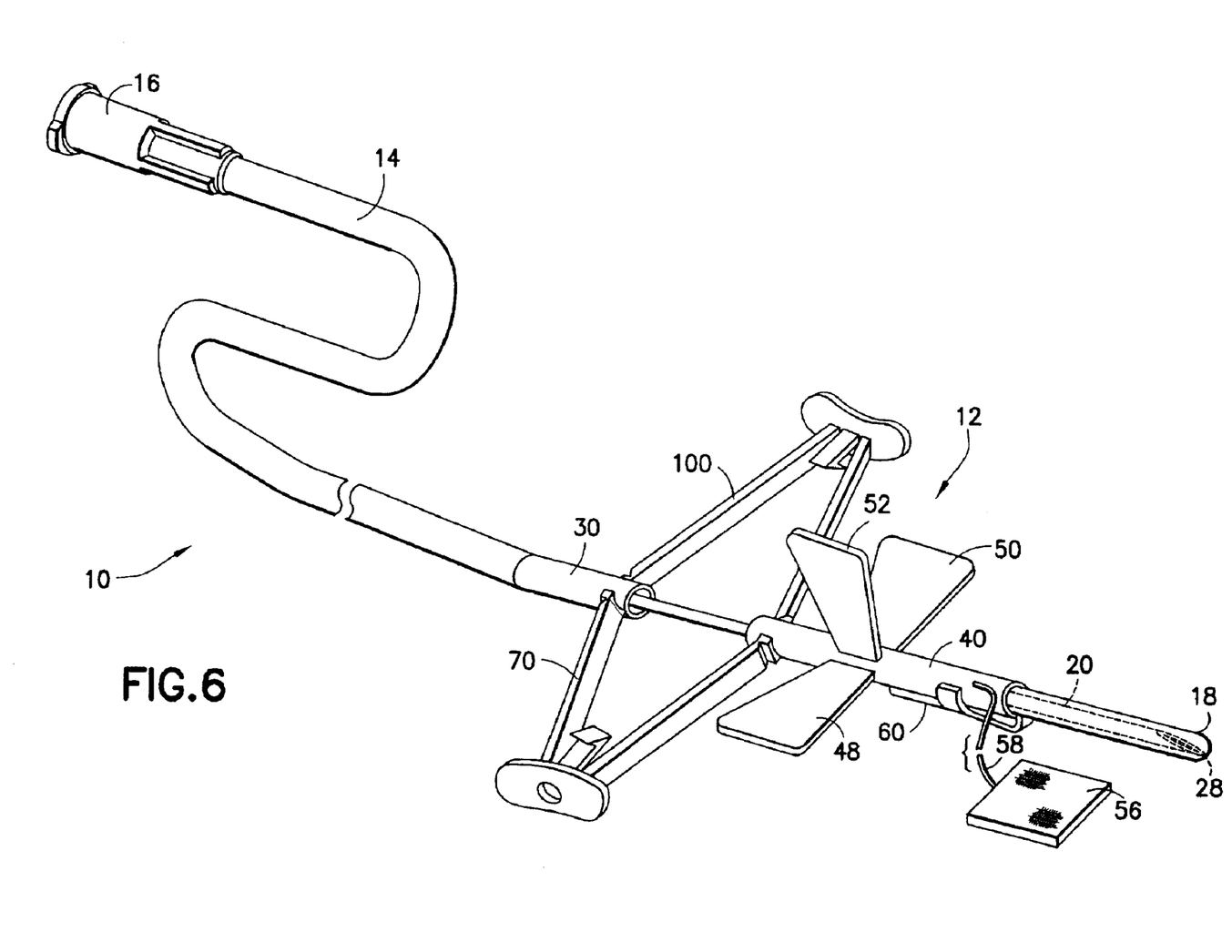
FIG. 6 is a perspective view of a blood collection set in accordance with the present invention.
Figure 7:
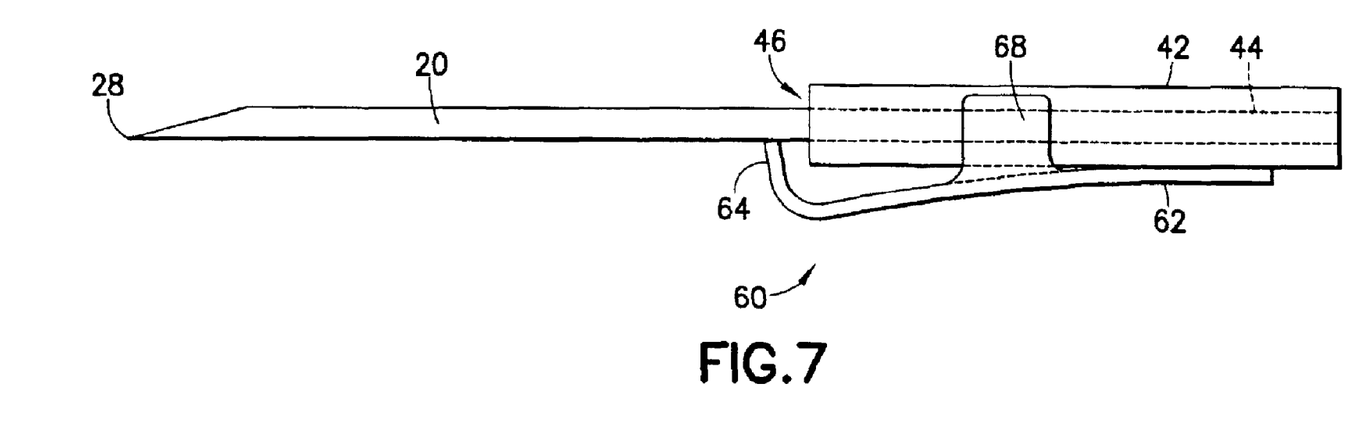
FIG. 7 is a side view of a tip guard useful in an alternate embodiment of the present invention.

Referring to the drawings in which like reference characters refer to like parts throughout the several views thereof, FIG. 6 illustrates a blood collection set 10 in accordance with the present invention and the related features. The present invention is generally described in terms of a blood collection set, and encompasses such a blood collection set as well as a shieldable needle assembly for use in such a blood collection set.

As shown in FIG. 6, blood collection set 10 includes a shieldable needle assembly 12, a flexible tube 14 extending from needle assembly 12 and a fixture 16 mounted to flexible tube 14. Shieldable needle assembly 12 of blood collection set 10 is shown in detail in FIGS. 1–5, and includes a needle cannula 20, a hub 30 and a shield member 40. Fixture 16 is connectable to a receptacle (not shown) for use in blood collection procedures, as is known in the art.

The shieldable needle assembly 12 of the blood collection set 10 includes a needle cannula 20. The needle cannula 20 has a proximal end 22 and an opposing distal end 24. The needle cannula 20 defines a lumen 26 extending through the needle cannula 20 from the proximal end 22 to the distal end 24. The distal end 24 of the needle cannula 20 is beveled to define a sharp puncture tip 28, such as an intravenous (IV) puncture tip. The puncture tip 28 is provided for insertion into a patient's blood vessel, such as a vein, and is, therefore, designed to provide ease of insertion and minimal discomfort during venipuncture. A removable protective needle cover 18 may be positioned over distal end 24 of needle cannula 20 for protection from puncture tip 28 prior to use of blood collection set 10.

The shieldable needle assembly 12 of the blood collection set 10 includes a hub member 30, a shield member 40, and at least one extendable member 70 and, preferably, a pair of extendable members 70, 100 connecting the hub member 30 and the shield member 40. The hub member 30, shield member 40, and extendable member 70 may be integrally formed as a unitary body, which is desirably molded from a thermoplastic material. However, the hub member 30, shield member 40, and extendable member 70 may be separate parts, which are preferably molded from thermoplastic material.

The hub member 30 has a proximal end 32 and a distal end 34, and is generally defined by a housing of a rigid tubular wall 36 extending from the proximal end 32 to the distal end 34. The tubular wall 36 defines an internal passage 38 extending from the proximal end 32 to the distal end 34. The hub member 30 is adapted to support the proximal end 22 of the needle cannula 20. In particular, the needle cannula 20 is positioned within the internal passage 38 defined by the tubular wall 36 of the hub member 30 and extends outward from the distal end 34 of the hub member 30. Preferably, the needle cannula 20 and hub member 30 are formed as separate parts that are fixedly attached and secured through an appropriate medical grade adhesive, by direct mechanical attachment, or other similar means.

Figure 1:
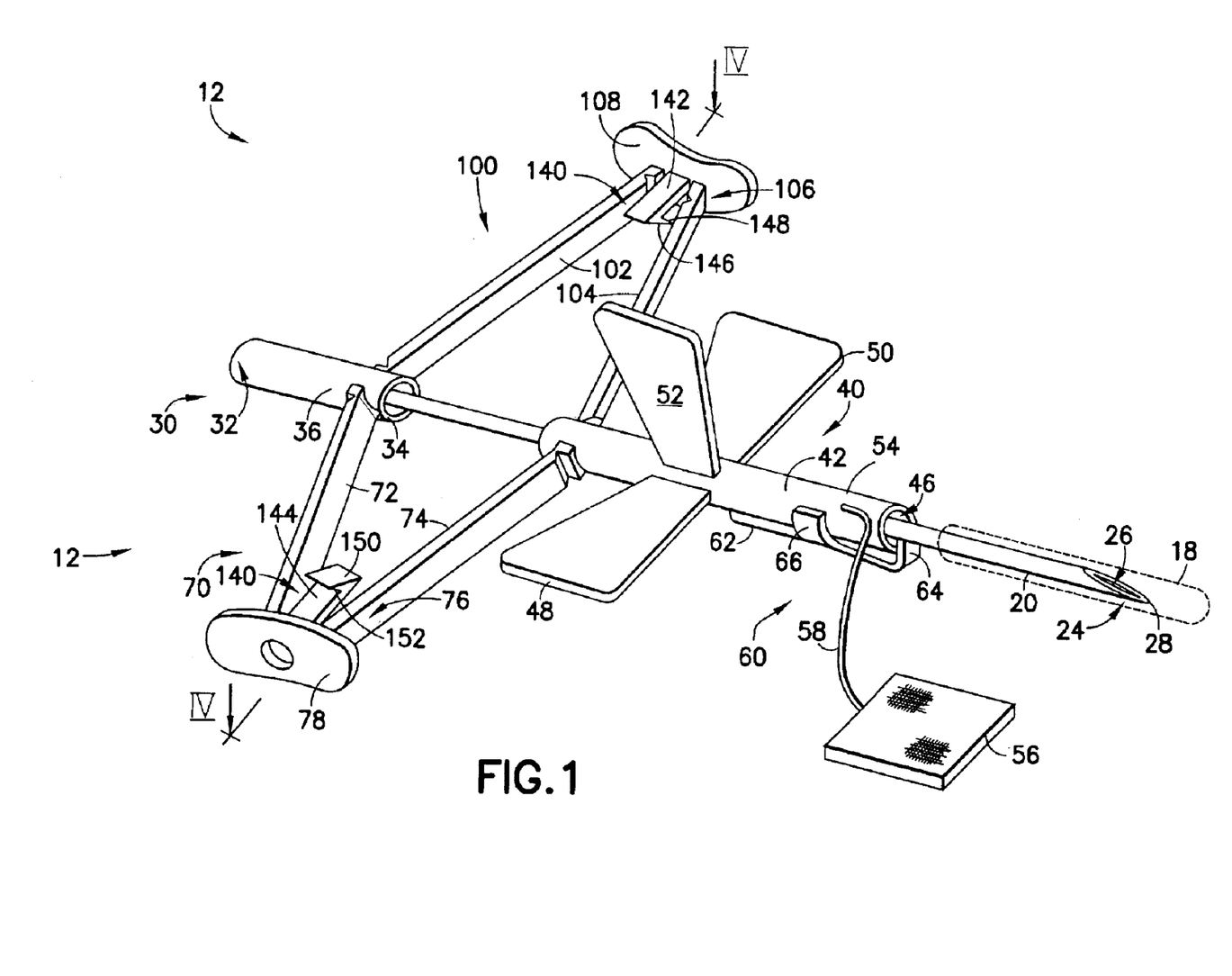
FIG. 1 is a perspective view of a needle assembly in accordance with the present invention shown in a first position for sampling.
Figure 2:
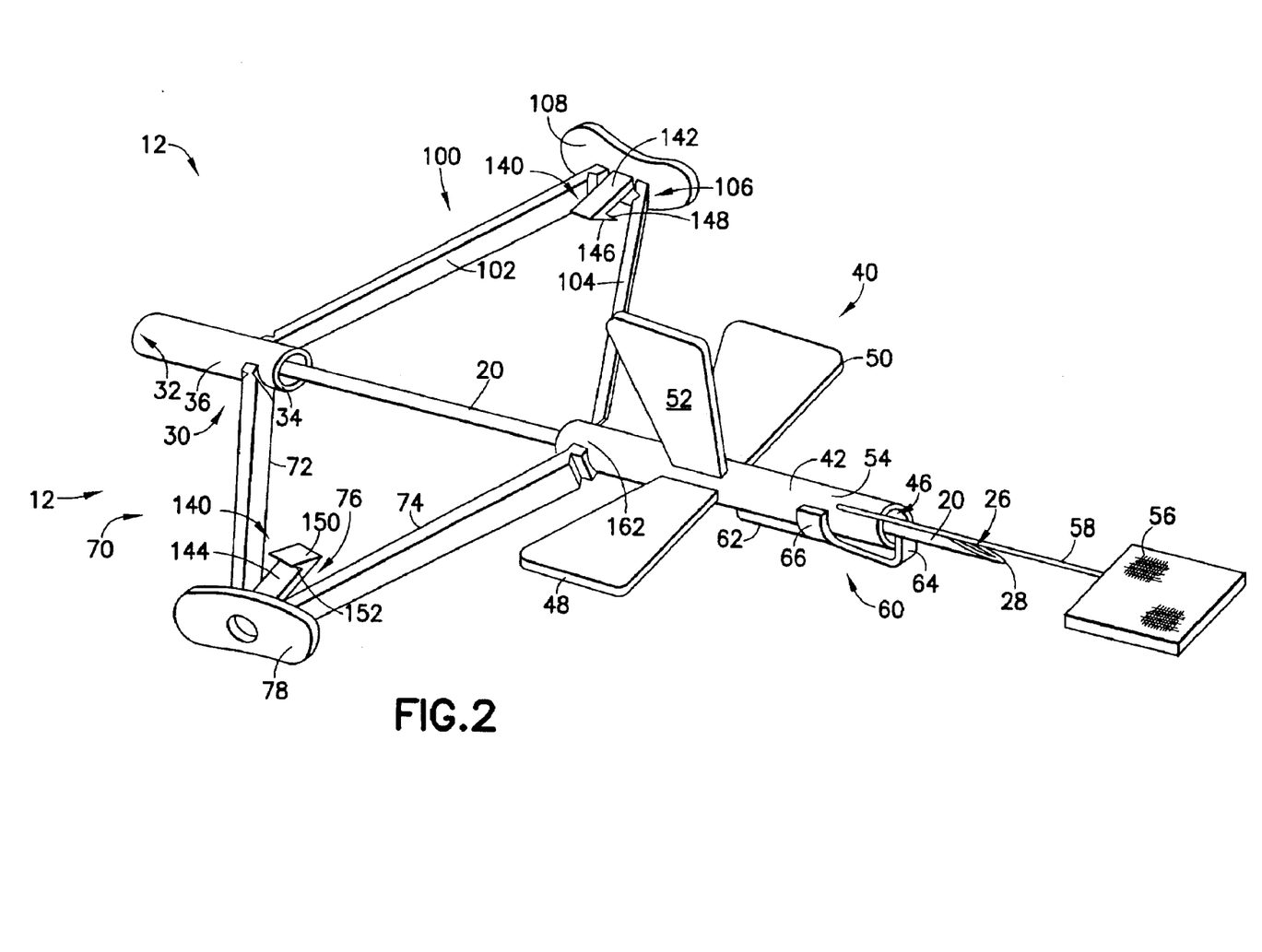
FIG. 2 is a perspective view of the needle assembly of FIG. 1 shown in a partially shielded position.
Figure 3:
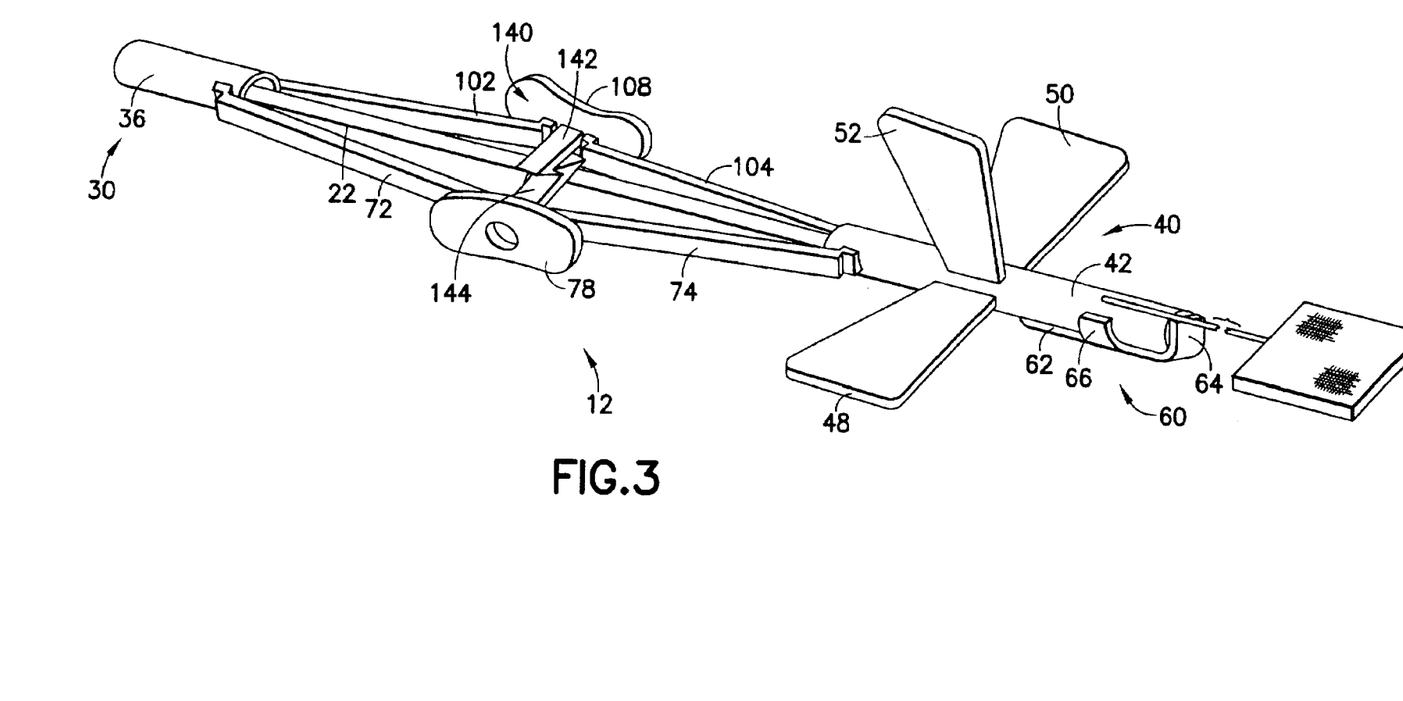
FIG. 3 is a perspective view of the needle assembly of FIG. 1 shown in a fully extended position.
Figure 4:
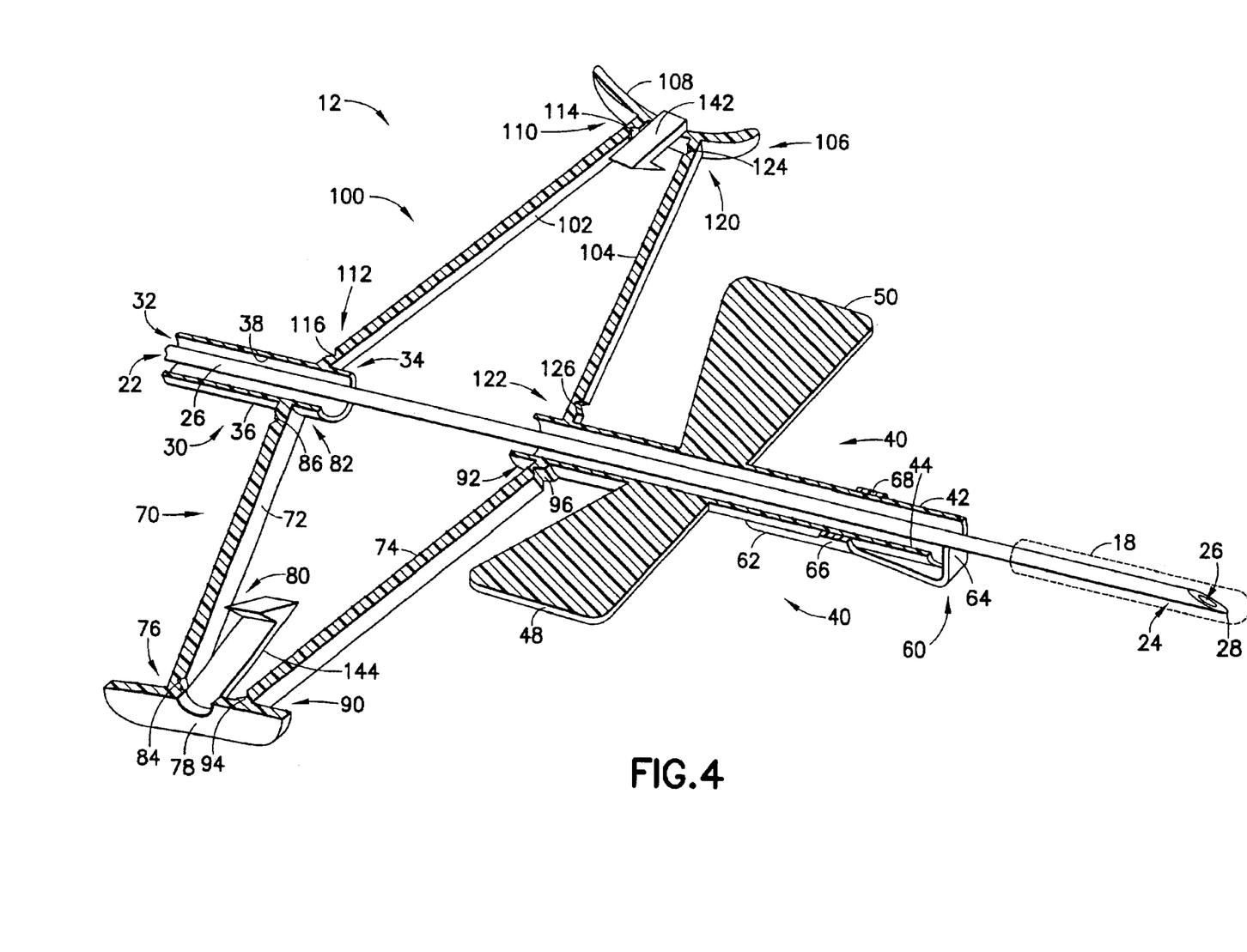
FIG. 4 is a cross section showing the inferior portion of the needle assembly taken along lines IV—IV of FIG. 1.
Figure 5:
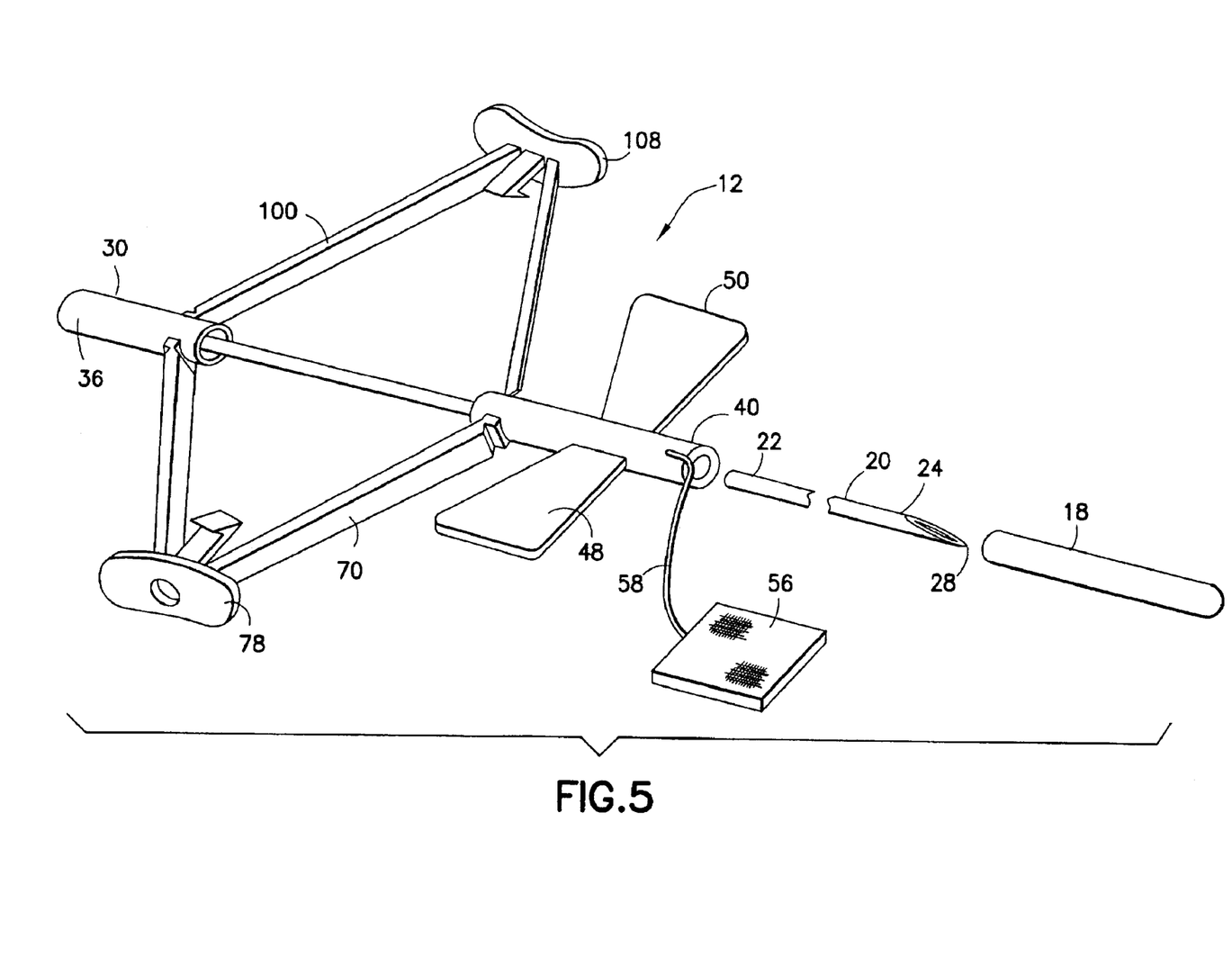
FIG. 5 is an exploded view of the needle assembly of FIG. 1.

The shield member 40 includes a housing 42 defining a central bore 44 having a distal opening 46 at one end thereof. The housing 42 of the shield member 40 extends co-axially about the needle cannula 20 and is in axial alignment with the internal passage 38 defined by the tubular wall 36 of the hub member 30. The shield member 40 and the hub member 30 are axially movable relative to each other in opposing axial directions, between a first position and a second position. In a first position, the shield member 40 is located in a proximal position adjacent the hub member 30, with the puncture tip 28 of the needle cannula 20 extending from the distal opening 46 of the shield member 40. In a second position, the shield member 40 is located in a distal position spaced from the hub member 30, with the needle cannula 20 contained entirely within the central bore 44 of the shield member 40, such that the puncture tip 28 of the needle cannula 20 does not extend beyond the distal opening 46 of the shield member 40 but is also contained within the shield member 40. As such, when the shield member 40 and the hub member 30 are in the first position, as shown in FIG. 1, the needle assembly 12 is in a sampling state, capable of venipuncture, as will be described in further detail. When the shield member 40 and the hub member 30 are in the second position, as shown in FIG. 3, the needle assembly 12 is in a shielded state after the safety feature of the needle assembly 12 has been activated to shield and protect the used puncture tip 28.

The shield member 40 may further include a pair of stabilizers in the form of wings 48, 50 that extend laterally from the housing 42 at opposing sides thereof. The lateral wings 48, 50 provide a butterfly-type wing assembly useful for positioning and placement of the needle assembly 12 and blood collection set 10 during a blood collection procedure. The shield member 40 may further include a dorsal wing 52 extending from the housing 42 and located between the lateral wings 48, 50. The dorsal wing 52 is preferably symmetrically positioned on the housing 42 between the lateral wings 48, 50. It is contemplated that the stabilizers or wings 48, 50 and the dorsal wing 52 may alternatively be positioned on the hub member 30 as opposed to the shield member 50.

The needle assembly 12 further includes a gauze pad 56 extending from and connected to the housing 42 of the shield member 40. The gauze pad 56 is a conventional gauze member as is known in the art for use in medical procedures, for example, in bandaging applications. The gauze member may be packaged within an appropriate packaging (not shown) in order to maintain a sterile environment prior to use.

The gauze pad 56 is connected to the shield member 40 through a connecting member in the form of a tether 58. The tether 58 is a flexible member which enables the gauze pad 56 to be moved and positioned at a desired location. The tether 58 may be, for example, a string which is connected at one end to gauze pad 56 and connected at the other end to a portion of the housing 42 of the shield member 40. The tether 58 may be connected to shield member 40 at any position, such as at the top portion 54 of the housing 42. Alternatively, the tether 58 may be connected to the shield member 40 at one of the wings 48, 50, or may be connected to the dorsal wing 52.

The tether 58 may be releasably connected between the gauze pad 56 and the shield member 40, such that the gauze pad 56 may be released from the needle assembly 12 upon exertion of a sufficient amount of force, as will be described in more detail herein. Such a releasable connection may be established, for example, by adhering the tether 58 to the housing 42 of shield member 40 with an adhesive which is capable of failing in its adhesive properties when the amount of force applied between the tether 58 and the shield member 40 exceeds a specific amount, thereby establishing a breakable bond therebetween.

The tether 58 should be sufficiently long enough to allow for positioning of the gauze pad 56 at a locating adjacent the puncture tip 28 of the needle cannula 20 when the hub member 30 and the shield member 40 are in the first position with the needle assembly 12 in the sampling state. In this manner, the gauze pad 56 can be placed directly over the puncture site during a medical procedure, such that the gauze pad 56 can be directly applied to the needle puncture wound during and after removal of the needle cannula 20 from the patient, without breaking the connection between the tether 58 and the shield member 40.

The tether 58 connected between the gauze pad 56 and the shield member 40 acts as a mechanism for activation of the shield member 40, thereby causing relative axial movement between the shield member 40 and the hub member 30 from the first position to the second position. In particular, by maintaining the gauze pad 56 in place while moving the hub member 30 of the needle assembly 12 away from the gauze pad 56, such as during removal from the patient, the tether 58 extends to a taut position. Since the tether 58 is connected to the shield member 40, it acts as an extension of the shield member 40, such that movement of the hub member 30 while maintaining the gauze pad 56 in place and extending the tether 58 causes the shield member 40 and the hub member 30 to move in opposing axial directions with respect to each other. Since needle cannula 20 is attached to hub member 30, such relative axial movement between the hub member 30 an the shield member 40 causes the needle cannula 20 to be retracted within the shield member 40, and/or causes the shield member 40 to move axially along the needle cannula 20. As such, the needle assembly 12 is caused to be moved from the sampling state, with the puncture tip 28 exposed from the distal end 46 of the shield member 40, to the shielded state, with shield member 40 covering puncture tip 28 of needle cannula 20.

Desirably, the tether 58 is of a length such that the tether 58 is extendable to a tightly stretched taut position when the gauze pad 56 is positioned directly adjacent the puncture tip 28 of the needle cannula 20 when the needle assembly 12 is in the sampling position. In this manner, removing the needle cannula 20 from the patient by pulling back on the hub member 30 will result in relative axial movement of the shield member 40 with respect to the hub member 30 during such withdrawal, due to the tether 58 being tightly stretched between the gauze pad 56 and the shield member 40. As such, the needle cannula 20 is retracted within the shield member 40 during withdrawal of the needle cannula 20 from the patient, thereby effectively encompassing and shielding puncture tip 28 of needle cannula 20 during the withdrawal procedure.

Optionally, a needle tip guard 60 is attached to the housing 42 of the shield member 40 distally forward of the lateral wings 48, 50 and dorsal wing 52. The tip guard 60 is provided to automatically cover the distal opening 46 of the central bore 44 of the housing 42 when the shield member 40 is moved to the fully extended position covering the puncture tip 28 of the needle cannula 20. The tip guard 60 is provided as a curved leaf spring of metal or the like having an axially extending spring leg 62, a generally right-angled locking plate 64, and a pair of clip legs 66, 68 forming a gripping collar for securely holding the tip guard 60 onto the housing 42 of the shield member 40. Operation of the tip guard 60 shown in FIGS. 1–5 will be discussed hereinafter.

As stated previously, the hub member 30 and shield member 40 are connected by at least one extendable member 70 and, preferably, a pair of extendable members 70, 100. The first extendable member 70 is comprised of a pair of folding legs, which include a first or proximal leg 72 and a second or distal leg 74. The first and second legs 72, 74 are connected by a hinged knee joint 76 that includes a fingerplate 78. The first leg 72 of the pair of folding legs is hingedly connected to the hub member 30 and the second leg 74 of the pair of legs is hingedly connected to the shield member 40. The first leg 72 includes a first end 80 and a second end 82. The first end 80 of the first leg 72 is connected to the fingerplate 78 by a hinged connection 84, and the second end 82 of the first leg 72 is connected to the hub member 30 by a hinged connection 86. Likewise, the second leg 74 includes a first end 90 and a second end 92. The first end 90 of the second leg 74 is connected by a hinged connection 94 to the fingerplate 78, and the second end 92 of the second leg 74 is connected by a hinged connection 96 to the shield member 40. Preferably, the fingerplate 78 of the knee joint 76 is concave to provide a convenient grasping location for the user of the needle assembly 12.

Similarly, the second extendable member 100 is comprised of a pair of folding legs, which include a first or proximal leg 102 and a second or distal leg 104. The first and second legs 102, 104 are connected by a hinged knee joint 106 that includes a fingerplate 108. The first leg 102 of the pair of folding legs is hingedly connected to the hub member 30 and the second leg 104 of the pair of legs is hingedly connected to the shield member 40. The first leg 102 includes a first end 110 and a second end 112. The first end 110 of the first leg 102 is connected to the fingerplate 106 by a hinged connection 114, and the second end 112 of the first leg 102 is connected to the hub member 30 by a hinged connection 116. Likewise, the second leg 104 includes a first end 120 and a second end 122. The first end 120 of the second leg 104 is connected by a hinged connection 124 to the fingerplate 108, and the second end 122 of the second leg 104 is connected by a hinged connection 126 to the shield member 40. Preferably, the fingerplate 108 of the knee joint 106 is also concave to provide a convenient grasping location for the user of the needle assembly 12. The respective folding legs 72, 74 and 102, 104 of the first and second extendable members 70, 100 are configured to generally extend laterally along the lateral sides of the needle assembly 12 when the shield member 40 is moved to the extended position.

The needle assembly 12 further includes means for preventing the shield member 40 from moving in an axial direction with respect to hub member 30 between the second shielded position and the first sampling position once the safety feature of the needle assembly 12 has been activated. For example, tip guard 60, discussed above, can function in this manner, with locking plate 64 preventing a re-exposure of the puncture tip 28 once it has been housed within shield member 40, as will be discussed in further detail herein. In addition to or instead of such a locking plate, a locking assembly 140 may be located on the extendable members 70, 100 for locking the shield member 40 in the extended position. In particular, the locking assembly 140 is preferably integrally formed as part of the knee joints 76, 106. The locking assembly 140 is formed by a locking member 142 and a locking catch member 144. The locking member 142 extends from the inside surface of fingerplate 108 and extends toward opposing fingerplate 78. The locking member 142 includes a sloped leading edge 146 located opposite from a substantially planar locking edge 148. The locking catch member 144 extends from the inside surface of opposing fingerplate 78 and is configured to cooperate with (i.e., receive) the locking member 142. The locking catch member 144 also includes a sloped leading edge 150 located opposite from a substantially planar locking edge 152, which is adapted to receive the locking edge 148 formed on the locking member 142. The operation of the locking assembly 140 will be discussed more fully hereinafter. It will be appreciated by those skilled in the art that the locations for the locking member 142 and the locking catch member 144 may be reversed.

As noted, a removable, protective needle cover 18 may be used to cover the distal end 24 of the needle cannula 20 and, more particularly, the puncture tip 28 of the needle cannula 20. The needle cover 18 is preferably positioned over the puncture tip 28 of the needle cannula 20 in a pre-use state of the needle assembly 12, wherein the shield member 40 is maintained in a proximal position adjacent hub member 30. The needle cover 18 is preferably an inexpensive, elongated plastic needle cover such as those commonly used as a needle protector in the medical field.

Moreover, in addition to being secured to the shield member 40 through tether 58, the gauze pad 56 may be secured directly to the needle assembly 12 in order to maintain it in place during packaging and venipuncture, and prior to use of the gauze pad 56. For example, gauze pad 56 may be secured to one of wings 48, 50, such as through attaching the sterile packaging of gauze pad 56 (not shown) directly thereto. Prior to activation of the safety feature of needle assembly 12, the gauze pad 56 can be removed from needle assembly 12, such as by opening the packaging secured to shield member 40 and removing the gauze pad 56 therefrom.

With the basic structure of the blood collection set 10 and needle assembly 12 now described, operation of the blood collection set 10 and needle assembly 12 will be described with reference to FIGS. 1–6. In use, blood collection set 10 is provided with needle assembly 12 assembled as described and including flexible tube 14 extending from needle assembly 12 and connected to fixture 16. After removing blood collection set 10 from its package, it can be assembled with other appropriate medical equipment for use. For example, an appropriate receptacle, such as a non-patient needle assembly and a needle holder, may be connected to blood collection set 10 through fixture 16, thereby providing fluid communication with lumen 26 through needle cannula 20.

The needle assembly 12 is preferably provided with the shield member 40 in the retracted state and the needle cover 18 positioned over the distal end 24 of the needle cannula 20. The shield member 40 is maintained in the retracted position through friction. To prepare for use of blood collection set 10, the user grasps blood collection set 10 at needle assembly 12 and removes the needle cover 18 to expose puncture tip 28 of needle cannula 20.

The medical practitioner then sterilizes the intended area of puncture on the patient's body, and can then urge puncture tip 28 at distal end 24 of needle cannula 20 into a targeted blood vessel of a patient. The user of the needle assembly 12 may then grasp the lateral wings 48, 50 and the dorsal wing 52 to assist in positioning the needle assembly 12 at the intended area of puncture on the patient's body. The lateral wings 48, 50 and the dorsal wing 52 are preferably made flexible so that they may be folded together to provide a convenient handle for manipulating the needle assembly 12. Once the puncture tip 28 of the needle cannula 20 is inserted into a blood vessel in the patient's body (i.e., venipuncture), the user may spread the lateral wings 48, 50 flat onto the patient's body and may tape them in place to maintain the positioning and placement of the needle assembly 12 during the medical procedure. The lateral wings 48, 50 in this configuration will also provide a barrier between the needle cannula 20 and the user's fingertips, which will help prevent an accidental needle-stick should the needle cannula 20 inadvertently retract from the site of insertion. The user of the needle assembly 12 may also grasp the fingerplates 78, 108 attached to the extendable members 70, 100 with his or her free hand to further assist in positioning and placing the needle assembly 12 at the intended site of insertion into the patient's body.

After completing the appropriate medical procedure such as infusion or blood collection, the user of the blood collection set 10 and needle assembly 12 may then activate the needle assembly 12 to shield the puncture tip 28 with the shield member 40. To accomplish this, the user grasps the gauze pad 56 while maintaining the needle cannula 20 within the puncture site. The gauze pad 56 is removed from any packaging material which may surround gauze pad 56 to maintain sterility. The user then places the gauze pad 56 over the puncture site on the patient while the needle cannula 20 is maintained within the patient. The user applies slight pressure to the puncture site through the gauze pad 56 with one hand, and grasps the needle assembly 12 at the hub member 30 in the other hand. The user can then slowly withdraw the needle cannula 20 from the patient by moving the hub member 30 in a direction away from the patient. Since the needle cannula 20 is connected to the hub member 30, such movement causes the needle cannula 20 to be withdrawn from the patient. The gauze pad 56 is maintained in place through one of the user's hands over the puncture site during this withdrawal, to cover the puncture wound when the needle cannula 20 is removed from the puncture site. Since the tether 58 is connected between the gauze pad 56 and the shield member 40 and since the shield member 40 is connected to the needle assembly 12, movement of the hub member 30 during such withdrawal causes the shield member 40 to initially move with the hub member 30 and the needle assembly 12. During such movement, the tether 58 is tightly extended to a taut condition between the gauze pad 56 and the shield member 40. At such point, the tightly extended tether 58 provides resistance to the shield member 40, and the shield member 40 stops moving in the direction of the hub member 30. Continuing movement of the hub member 30 while maintaining the gauze pad 56 in place with the tether 58 in a taut condition will cause the hub member 30 and the shield member 40 to move in opposing axial directions with respect to each other, thereby causing the needle cannula 20 and the puncture tip 28 to axially move within the housing 42 of the shield member 40.

As the needle cannula 20 is withdrawn into the shield member 40, the locking member 142 and locking catch member 144 extending from the respective fingerplates 78, 108 of the extendable members 70, 100 begin to move toward one another. As the shield member 40 travels along the needle cannula 20 toward its shielded position, the sloped leading edge 146 of the locking member 142 slidably engages the sloped leading edge 150 of the locking catch member 144. As the shield member 40 reaches its fully shielding position, the locking edge 148 of the locking catch member 144 snaps into engagement with the locking edge 152 of the locking catch member 144 to secure the shield member 40 in the shielded position. Once the locking member 142 and locking catch member 144 are in engagement, the extendable members 70, 100 will be prevented from moving transversely away from the lateral sides of the needle assembly 12. Thus, the locking assembly 140, once engaged, prevents the re-emergence of the puncture tip 28 of the needle cannula 20 from the shield member 40.

Figure 8:
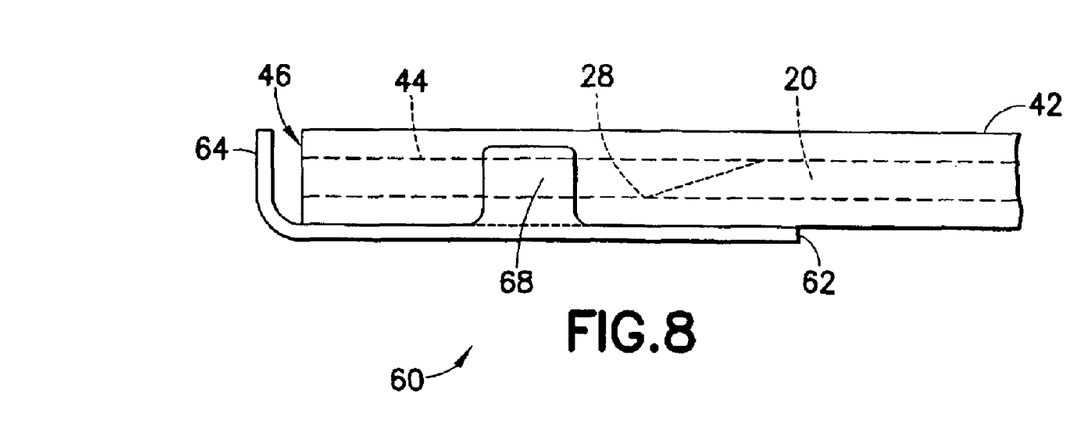
FIG. 8 is a side view of the tip guard of FIG. 8 shown in a shielded position covering a distal end of the needle assembly.

The tip guard 60 attached to the housing 42 of the shield member 40 will automatically cover the distal opening 46 of the central bore 44 once the needle cannula 20 is fully covered by the shield member 40. In particular, as shown in FIGS. 8 and 9, when the shield member 40 is in the first position, the needle cannula 20 extends outward from the housing 42 of the shield member 40 and the locking plate 64 of the tip guard 60 is biased into engagement with the needle cannula 20. In particular, the spring leg 62 biases the locking plate 64 into engagement with the needle cannula 20. As the needle cannula 20 is retracted within the shield member 40, the locking plate 64 slides along a bottom surface of the needle cannula 20 until the needle cannula 20 is fully covered by the shield member 40. Once the locking plate 64 is no longer in engagement with the needle cannula 20, the axially extending spring leg 62 causes the locking plate 64 to automatically extend over the distal opening 46 to the central bore 44 of the housing 42. The tip guard 60 fully covers the distal opening 46 to the central bore 44 of the housing 42, thereby preventing any re-emergence of the needle cannula 20. The blood collection set 10 and needle assembly 12 are now placed in a safety state. The tether 58 can be released from the shield member 40 by pulling the tether 58 and the needle assembly 12 apart, to break the adhesive bond therebetween. The gauze pad 56 can then be taped into place as a bandage over the puncture wound. The needle assembly 12 may then be safely disposed of as medical waste.

The blood collection set of the present invention incorporating the needle assembly described herein is particularly useful in that activation of the safety feature is accomplished without any additional effort on the part of the medical practitioner, apart from the normal removal of a needle cannula and covering of the puncture site. In particular, since a medical practitioner typically covers the puncture wound of a patient with gauze to prevent bleeding after a venipuncture procedure while withdrawing the needle from the patient, and since the present invention provides a needle assembly with the gauze pad 56 connected to the shield member 40 through the tether 58, shielding of the used needle cannula 20 and puncture tip 28 is accomplished through such typical techniques. Thus, while activation of the needle assembly of the present invention requires two hands, there is no additional effort required to shield the needle beyond that which would typically be employed in removing a needle cannula from a patient.

While the needle assembly of the present invention has been described in terms of one embodiment for use in connection with a blood collection system, it is further contemplated that the needle assembly could be used with other medical procedures, such as in conjunction with a conventional intravenous infusion set, which are well known in the art for use with needle assemblies.

While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed:

1. A needle assembly, comprising:
   a needle cannula having a proximal end and a distal end with a puncture tip;
   a hub member supporting the proximal end of the needle cannula;
   a shield member extending co-axially about the needle cannula, said hub member and said shield member adapted for relative axial movement with respect to each other between a first position in which said needle assembly is in a sampling state with said puncture tip of said needle cannula exposed from said shield member, and a second position in which said needle assembly is in a shielded state with said puncture tip of said needle cannula contained within said shield member; and a gauze member extending from and connected to said shield member through a connecting member, said connecting member extendable to a taut position when said gauze member is adjacent said puncture tip and said hub member and said shield member are in said first position, wherein movement of said hub member away from said gauze member when said connecting member is extended to said taut position causes said relative axial movement of said shield member and said hub member between said first position and said second position, thereby shielding said needle cannula.

2. A needle assembly as in claim 1, wherein said connecting member comprises a string.

3. A needle assembly as in claim 1, wherein said gauze member is removably connected to said shield member.

4. A needle assembly as in claim 1, wherein said connecting member is attached to a top portion of said shield member.

5. A needle assembly as in claim 1, further comprising a pair of wing members extending laterally from opposing sides of said needle assembly.

6. A needle assembly as in claim 5, wherein said pair of wing members extend laterally from opposing sides of said shield member.

7. A needle assembly as in claim 1, further comprising structure for preventing said shield member from extending beyond said puncture tip.

8. A needle assembly as in claim 1, further comprising at least one extendable member interconnecting the hub member and the shield member.

9. A needle assembly as in claim 8, further comprising a second extendable member interconnecting the hub member and the shield member and located opposite from the first extendable member.

10. A needle assembly as in claim 9, wherein the extendable members are each comprised of a pair of folding legs connected by a hinged knee joint, with one leg of the pair of legs for each extendable member hingedly connected to the hub member and the other leg of the pair of legs for each of extendable member hingedly connected to the shield member.

11. A needle assembly as in claim 1, further comprising structure for preventing relative axial movement of said hub member and said shield member between said second position and said first position.

12. A needle assembly as in claim 11, wherein said shield member further comprises a tip guard including a tip guard housing formed from a plastic material, a metallic spring clip being mounted to said housing, said spring clip being biased against said needle cannula when shield member is in said retracted position and being resiliently moved over said distal end of said needle cannula when said needle assembly is in said shielded state.

13. A shieldable blood collection set comprising:

a flexible tube having opposed first and second ends, said first end of said flexible tube adapted for connecting the blood collection set to a receptacle;

a hub including an elongated tubular body having an outer surface, a proximal end, a distal end and a passageway extending through said hub, said proximal end of said hub mounted to said second end of said flexible tube;

a needle cannula extending from said distal end of said hub, said needle cannula including a proximal end and a distal end having a puncture tip;

a hollow shield comprising a housing having a proximal end, a distal end and a passageway extending therethrough, said shield co-axially surrounding said needle cannula, said shield and said hub adapted for relative axial movement between a first position in which said puncture tip of said needle cannula is exposed from said distal end of said shield, and a second position in which said shield covers said puncture tip of said needle cannula; and a gauze member extending from and connected to said shield through a tether, said tether extendable to a taut position when said gauze member is adjacent said puncture tip and said shield and said hub are in said first position, wherein movement of said hub away from said gauze member when said tether is extended to said taut position causes said relative axial movement of said shield and said hub between said first position and said second position.

14. A blood collection set as in claim 13, wherein said gauze member is removably connected to said shield through said tether.

15. A blood collection set as in claim 13, wherein said tether is connected to a top portion of said housing of said shield.

16. A blood collection set as in claim 13, further comprising a pair of wing members extending laterally from opposing sides of said blood collection set.

17. A blood collection set as in claim 13, further comprising at least one extendable member interconnecting the hub member and the shield member.

18. A method for shielding a puncture tip in a needle assembly comprising:

providing a needle assembly comprising a hub member including a needle cannula extending therefrom, said needle cannula having a puncture tip at the end thereof; a shield member extending co-axially about the needle cannula, said shield member and said hub member axially movable with respect to each other; and a gauze member extending from and connected to the shield member through a connecting member; and maintaining said gauze member in a position adjacent said puncture tip while simultaneously moving said hub member in an axial direction away from said gauze member, thereby causing said connecting member to be extended to a taut position and causing said hub member and said needle cannula to axially move with respect to said shield member from a first position in which said puncture tip of said needle cannula is exposed from said shield member to a second position in which said shield member covers said puncture tip of said needle cannula.

19. A method as in claim 18, wherein said gauze member is removably connected to said shield member.

20. A method as in claim 18, wherein said needle assembly includes at least one extendable member interconnecting the hub member and the shield member.

\* \* \* \* \*